United States Patent
Castro Pineiro et al.

(10) Patent No.: US 7,049,296 B2
(45) Date of Patent: May 23, 2006

(54) GAMMA-SECRETASE INHIBITORS

(75) Inventors: Jose Luis Castro Pineiro, Bishops Stortford (GB); Adrian Leonard Smith, Simi Valley, CA (US); Graeme Irvine Stevenson, Saffron Walden (GB)

(73) Assignee: Merck Sharp & Dohme Ltd., Hertfordshire (*) Notice: Subject to any disclaimer, the term of this patent is extended or adjusted under 35 U.S.C. 154(b) by 215 days.

(21) Appl. No.: 10/204,962

(22) PCT Filed: Feb. 28, 2001

(86) PCT No.: PCT/GB01/00855

§ 371 (c)(1),
(2), (4) Date: Aug. 23, 2002

(87) PCT Pub. No.: WO01/66564

PCT Pub. Date: Sep. 13, 2001

(65) Prior Publication Data

US 2003/0055005 A1  Mar. 20, 2003

(30) Foreign Application Priority Data

Mar. 3, 2000  (GB) ................... 0005251.4

(51) Int. Cl.
*A61K 38/05* (2006.01)
*C07C 271/00* (2006.01)
*C07K 5/06* (2006.01)

(52) U.S. Cl. ............... 514/19; 548/311.1; 548/339.1; 560/24

(58) Field of Classification Search ............ 514/2; 530/300, 323
See application file for complete search history.

(56) References Cited

U.S. PATENT DOCUMENTS 6,756,511 B1 * 6/2004 Castro Pineiro et al. .... 564/153

FOREIGN PATENT DOCUMENTS

EP  0-554-400 B1 * 7/1997 ............... 530/300
WO  WO 92/08698  5/1992

OTHER PUBLICATIONS

MM Esiri, SC Biddolph, and CS Morris. Prevalence of alzheimer plaques in AIDS. (1998) J. Neurol. Neurosurg. Psychiatry, 65, 29-33.*
WebMD Alzheimer's Disease: treatment overview. Http://my.webmd.com/content/article/71/81399.htm. Accessed Feb. 22, 2005. 2 pages.*
ADEAR Alzheimer's Disease Medications fact sheet. NIH Publication 03-3431. Alzheimer's Disease Education & Referral Center. National Institute on Aging, NIH, US Dept HHS. Jul. 2004. 6 pages.*
C Ballard, et al. Quetiapine and rivastigmine and cognitive decline in Alzheimer's disease : randomized double blind placebo controlled trial. British Medical Journal. (2005) Feb. 18, 5 pages.*
ET Sutton, et al. B-amyloid-induced endothelial necrosis and inhibition of nitric oxide production. Experimental Cell Research (1997) 230, pp. 368-376.*
H Steiner et al.: Biochemistry vol. 38, No. 44, 1999, pp. 14600-14605.

* cited by examiner

*Primary Examiner*—Bruce R. Campell
*Assistant Examiner*—Andrew D. Kosar
(74) *Attorney, Agent, or Firm*—John C. Todaro; Melvin Winokur

(57) ABSTRACT

Urea derivatives of formula I are disclosed: The compounds are inhibitors of γ-secretase, and hence useful in the treatment or prevention of Alzheimer's Disease (I)

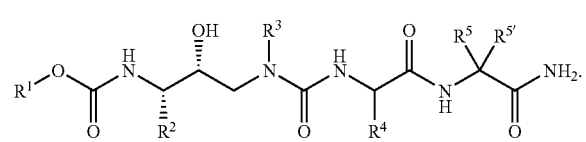

6 Claims, No Drawings

GAMMA-SECRETASE INHIBITORS

CROSS REFERENCE TO RELATED APPLICATIONS

This application is a U.S. National Phase application under 35 U.S.C. § 371 of PCT Application No. PCT/GB01/00200, filed Jan. 19, 2001, which claims priority under 35 U.S.C. § 119 from GB Application No. 0001589.1, filed Jan. 24, 2000, and from GB Application No. 0003767.1, filed Feb. 17, 2000.

The present invention relates to compounds, their salts, pharmaceutical compositions comprising them, processes for making them and their use in treating Alzheimer's Disease.

Alzheimer's Disease (AD) is characterised by the abnormal deposition of amyloid in the brain in the form of extra-cellular plaques and intra-cellular neurofibrillary tangles. The rate of amyloid accumulation is a combination of the rates of formation, aggregation and egress from the brain. It is generally accepted that the main constituent of amyloid plaques is the 4 kD amyloid protein (βA4, also referred to as Aβ, β-protein and βAP) which is a proteolytic product of a precursor protein of much larger size. The ragged $NH_2$- and COOH-termini of the native Aβ amyloid indicates that a complex mechanism of proteolysis is involved in its biogenesis.

The amyloid precursor protein (APP or AβPP) has a receptor-like structure with a large ectodomain, a membrane spanning region and a short cytoplasmic tail. Different isoforms of APP result from the alternative splicing of three exons in a single gene and have 695, 751 and 770 amino acids respectively.

The Aβ domain encompasses parts of both extra-cellular and transmembrane domains of APP, thus its release implies the existence of two distinct proteolytic events to generate its $NH_2$- and COOH-termini. At least two secretory mechanisms exist which release APP from the membrane and generate the soluble, COOH-truncated forms of APP ($APP_s$). Proteases which release APP and its fragments from the membrane are termed "secretases". Most $APP_s$ is released by a putative α-secretase which cleaves within the Aβ domain (between residues $Lys^{16}$ and $Leu^{17}$) to release $α-APP_s$ and precludes the release of intact Aβ. A minor portion of $APP_s$ is released by a β-secretase, which cleaves near the $NH_2$-terminus of Aβ and produces COOH-terminal fragments (CTFs) which contain the whole Aβ domain. Finding these fragments in the extracellular compartment suggests that another proteolytic activity (γ-secretase) exists under normal conditions which can generate the COOH-terminus of Aβ.

It is believed that γ-secretase itself depends for its activity on the presence of presenilin-1. In a manner that is not fully understood presenilin-1 appears to undergo autocleavage.

The compounds of the present invention are useful for treating AD by inhibiting the activity of the putative γ-secretase thus preventing the formation of insoluble Aβ and arresting the production of Aβ. Further, some of the present compounds also stabilise full-length presenilin-1.

In a further aspect some of the compounds of the present application are useful as inhibitors of presenilin-1 cleavage.

The present invention accordingly provides a compound of formula I or a pharmaceutically acceptable salt thereof:

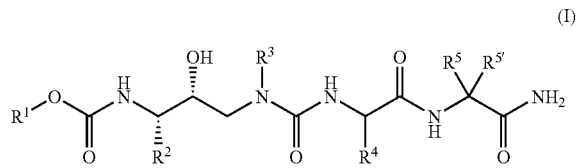

(I)

wherein:
$R^1$ is (1) $C_{1-10}$alkyl, $C_{2-20}$alkenyl or $C_{2-10}$alkynyl optionally substituted with one to three substituents independently chosen from:
(i) hydroxy;
(ii) carboxy;
(iii) halogen;
(iv) $C_{1-4}$alkoxy;
(v) $C_{1-4}$alkoxycarbonyl;
(vi) —$NR^6R^7$ wherein $R^6$ and $R^7$ are independently chosen from hydrogen, $C_{1-5}$alkyl and $C_{1-5}$alkoxy $C_{1-5}$alkyl;
(vii) —$CONR^6R^7$ or $OCONR^6R^7$ wherein $R^6$ and $R^7$ are independently as defined above;
(viii) —$N(R^8)QR^9$ wherein:
  Q is C(O), C(S), $SO_2$ or C(NH);
  $R^8$ is hydrogen or $C_{1-4}$alkyl; and
  $R^9$ is hydrogen, $C_{1-4}$alkyl, $C_{1-4}$alkoxy, amino, $C_{1-4}$alkylamino di($C_{1-4}$alkyl)amino wherein each alkyl group is independently chosen;
(ix) $C_{3-7}$cycloalkyl;
(x) phenyl or naphthyl; a five-membered heterocyclic ring containing 1, 2, 3 or 4 heteroatoms independently chosen from O, N and S, at most one of the heteroatoms being O or S; a six-membered heterocyclic ring containing 1, 2 or 3 nitrogen atoms; each of which is optionally substituted by one to three groups independently chosen from:
  (a) halogen, cyano and nitro,
  (b) hydroxy,
  (c) $C_{1-4}$alkyl, $C_{2-4}$alkenyl and $C_{2-4}$alkynyl,
  (d) $C_{1-4}$alkoxy,
  (e) $NR^6R^7$ wherein $R^6$ and $R^7$ are independently as defined above,
  (f) $CO_2R^8$ wherein $R^8$ is independently as defined above,
  (g) $CONR^6R^7$ or $OCONR^6R^7$ wherein $R^6$ and $R^7$ are independently as defined above,
  (h) $SO_2NR^6R^7$ wherein $R^6$ and $R^7$ are independently as defined above,
  (i) $CH_2NR^6R^7$ wherein $R^6$ and $R^7$ are independently as defined above,
  (j) $N(R^8)COR^{8'}$ wherein $R^8$ is independently as defined above and $R^{8'}$ is independently as defined for $R^8$, and
  (k) $NR^8SO_2R^{8'}$ wherein $R^8$ and $R^{8'}$ are independently as defined above; or
(2) phenyl or naphthyl; a five-membered heterocyclic ring containing 1, 2, 3 or 4 heteroatoms independently chosen from O, N and S, at most one of the heteroatoms being O or S; a six-membered heterocyclic ring containing 1, 2 or 3 nitrogen atoms; each of which is optionally substituted by one to three groups independently chosen from:

(a) halogen, cyano and nitro,
(b) hydroxy,
(c) $C_{1-4}$alkyl, $C_{2-4}$alkenyl and $C_{2-4}$alkynyl,
(d) $C_{1-4}$alkoxy,
(e) $NR^6R^7$ wherein $R^6$ and $R^7$ are independently as defined above,
(f) $CO_2R^8$ wherein $R^8$ is independently as defined above,
(g) $CONR^6R^7$ or $OCONR^6R^7$ wherein $R^6$ and $R^7$ are independently as defined above,
(h) $SO_2NR^6R^7$ wherein $R^6$ and $R^7$ are independently as defined above,
(i) $CH_2NR^6R^7$ wherein $R^6$ and $R^7$ are independently as defined above,
(j) $N(R^8)COR^{8'}$ wherein $R^8$ and $R^{8'}$ are independently as defined above, and
(k) $NR^8SO_2R^{8'}$ wherein $R^8$ and $R^{8'}$ are independently as defined above;

$R^2$ and $R^3$ are independently chosen from $C_{1-10}$alkyl, $C_{1-10}$alkoxy, $C_{2-10}$alkenyl, $C_{2-10}$alkenyloxy, $C_{2-10}$alkynyl or $C_{2-10}$alkynyloxy; phenyl; naphthyl; a five-membered heteroaromatic ring containing 1, 2, 3 or 4 heteroatoms independently chosen from O, N and S, at most one of the heteroatoms being O or S; a six-membered heteroaromatic ring containing 1, 2 or 3 nitrogen atoms; and a group $(CH_2)_pQ^1$ wherein $Q^1$ is phenyl, naphthyl, a five-membered heteroaromatic ring containing 1, 2, 3 or 4 heteroatoms independently chosen from O, N and S, at most one of the heteroatoms being O or S, and a six-membered heteroaromatic ring containing 1, 2 or 3 nitrogen atoms; and wherein each of $R^2$ and $R^3$ is independently optionally substituted by one to three groups independently chosen from:
(a) halogen, cyano and nitro,
(b) hydroxy,
(c) $C_{1-6}$alkyl, $C_{2-6}$ alkenyl and $C_{2-6}$alkynyl,
(d) $C_{1-6}$alkoxy and phenoxy each of which is optionally substituted by one to three halogen atoms,
(e) $NR^6R^7$ wherein $R^6$ and $R^7$ are independently as defined above,
(f) $CO_2R^8$ wherein $R^8$ is independently as defined above,
(g) $CONR^6R^7$ or $OCONR^6R^7$ wherein $R^6$ and $R^7$ are independently as defined above,
(h) $SO_2NR^6R^7$ wherein $R^6$ and $R^7$ are independently as defined above,
(i) $CH_2NR^6R^7$ wherein $R^6$ and $R^7$ are independently as defined above,
(j) $N(R^8)COR^{8'}$ wherein $R^8$ and $R^{8'}$ are independently as defined above,
(k) $NR^8SO_2R^{8'}$ where $R^8$ and $R^{8'}$ are independently as defined above;
alternatively $R^3$ may be hydrogen;

$R^4$ and $R^5$ are independently chosen from hydrogen, $C_{1-6}$alkyl optionally substituted by halogen, hydroxy, thiol, amino, $C_{1-4}$alkoxy, $C_{1-4}$ alkylthio, carboxy, $C_{1-4}$alkoxycarbonyl and $(CH_2)_qQ^2$ wherein $Q^2$ is a five-membered unsaturated heterocycle containing 1, 2, 3 or 4 heteroatom optionally chosen from O, N, and S providing that not more than one heteroatom is O or S, a six-membered unsaturated heterocycle containing 1, 2 or 3 N atoms, phenyl, naphthyl or a fused ring which is indolyl, each of the foregoing rings being optionally substituted with one to three groups independently chosen from hydroxy, $C_{1-4}$alkyl, $C_{1-4}$alkoxy, thiol, $C_{1-4}$alkylthio, halogen, amino, carboxy, amido, $CO_2H$ and $—NHC(NH_2)_2$; and $R^{5'}$ is a hydrogen atom;
alternatively $R^5$ and $R^{5'}$ together represent an oxo group;
p is zero, one, two or three; and
q is zero, one, two or three;
with the proviso that no carbon atom is substituted by more than one hydroxy group.

In one embodiment the compounds of the present invention are of formula I':

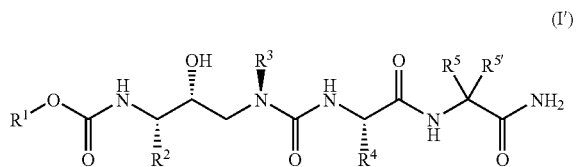

(I')

where $R^1$, $R^2$, $R^3$, $R^4$ and $R^5$ are as defined above.

In another embodiment there are provided compounds of formula I":

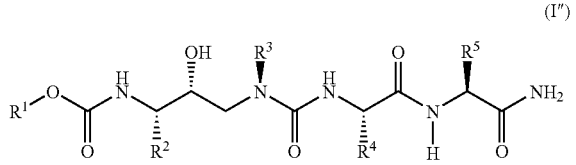

(I")

where $R^1$, $R^2$, $R^3$, $R^4$ and $R^5$ are as defined above.

The following preferred definitions of substituents apply to each of the formulae I, I' and I" which refer to those substituents.

Preferably $R^1$ is
(1) $C_{1-10}$alkyl, $C_{2-10}$alkenyl or $C_{2-10}$alkynyl optionally substituted with one to three substituents independently chosen from:
    (i) hydroxy;
    (ii) halogen;
    (iii) amino;
    (iv) $C_{1-4}$alkoxy; and
    (v) phenyl which is optionally substituted by one or two groups independently chosen from:
        (a) halogen, cyano and nitro,
        (b) hydroxy,
        (c) $C_{1-4}$alkyl, $C_{2-4}$alkenyl and $C_{2-4}$alkynyl,
        (d) $C_{1-4}$alkoxy and
        (e) amino; or
(2) phenyl which is optionally substituted by one or two groups independently chosen from:
    (a) halogen, cyano and nitro,
    (b) hydroxy,
    (c) $C_{1-4}$alkyl, $C_{2-4}$alkenyl and $C_{2-4}$alkynyl,
    (d) $C_{1-4}$alkoxy and
    (e) amino.

Most preferably $R^1$ is $C_{1-6}$alkyl or benzyl optionally substituted by one or two groups chosen from halogen, cyano, nitro, hydroxy, $C_{1-4}$alkyl, $C_{2-4}$alkenyl, $C_{2-4}$alkynyl, $C_{1-4}$alkoxy and amino.

$R^1$ may be unsubstituted benzyl or unsubstituted $C_{1-6}$alkyl such as t-butyl.

When $R^1$ is a heterocyclic ring it may be saturated, partially saturated or unsaturated. Preferably the heterocyclic ring is a heteroaromatic ring.

R² and R³ may be independently chosen from phenyl; naphthyl; a five-membered heteroaromatic ring containing 1, 2, 3 or 4 heteroatoms independently chosen from O, N and S, at most one of the heteroatoms being O or S; a six-membered heteroaromatic ring containing 1, 2 or 3 nitrogen atoms; and a group $(CH_2)_pQ^1$ wherein $Q^1$ is phenyl; naphthyl; a five-membered heteroaromatic ring containing 1, 2, 3 or 4 heteroatoms independently chosen from O, N and S, at most one of the heteroatoms being O or S; and a six-membered heteroaromatic ring containing 1, 2 or 3 nitrogen atoms; and wherein each of R² and R³ is independently optionally substituted by one to three groups independently chosen from:

(a) halogen, cyano and nitro,
(b) hydroxy,
(c) $C_{1-4}$alkyl, $C_{2-4}$alkenyl and $C_{2-4}$alkynyl,
(d) $C_{1-6}$alkoxy and phenoxy each of which is optionally substituted by one to three halogen atoms,
(e) $NR^6R^7$ wherein $R^6$ and $R^7$ are independently as defined above,
(f) $CO_2R^8$ wherein $R^8$ is independently as defined above,
(g) $CONR^6R^7$ wherein $R^6$ and $R^7$ are independently as defined above,
(h) $SONR^6R^7$ wherein $R^6$ and $R^7$ are independently as defined above,
(i) $CH_2NR^6R^7$ wherein $R^6$ and $R^7$ are independently as defined above,
(j) $N(R^8)COR^{8'}$ wherein $R^8$ and $R^{8'}$ are independently as defined above,
(k) $NR^8SO_2R^{8'}$ where $R^8$ and $R^{8'}$ are independently as defined above.

More preferably R² and R³ are $(CH_2)_pQ^1$.

Preferably $Q^1$ is phenyl, pyridyl or furyl optionally substituted by one or two groups independently chosen from:
(a) halogen, cyano and nitro,
(b) hydroxy,
(c) $C_{1-3}$alkyl, $C_{2-3}$alkenyl and $C_{2-3}$alkynyl,
(d) $C_{1-3}$alkoxy and phenoxy each of which is optionally substituted by up to three halogen atoms,
(e) amino.

Particularly $Q^1$ is phenyl, pyridyl or furyl optionally substituted by chlorine, trifluoromethoxy or phenoxy.

R³ is particularly benzyl, phenethyl, 4-phenoxyphenethyl, 4-chlorobenzyl, 3-chlorobenzyl, 2-chlorobenzyl, 2-pyridylmethyl, 2-furyl or 4-trifluoromethoxybenzyl.

In one embodiment R² is benzyl.

Preferably R⁴ and R⁵ are independently chosen from optionally substituted $C_{1-6}$alkyl and $(CH_2)_qQ^2$. More preferably R⁴ and R⁵ are independently chosen from $C_{1-6}$alkyl and $(CH_2)_qQ^2$.

Preferably $Q^2$ is optionally substituted phenyl. More preferably $Q^2$ is phenyl.

In particular R⁴ and R⁵ are independently chosen from isobutyl, benzyl, n-butyl, n-propyl, methyl, s-butyl, isopropyl and phenyl.

In one embodiment $R^5$ and $R^{5'}$ are an oxo group.

p is preferably one, two or three, especially one or two.

q is preferably zero or one.

Thus a subclass of compounds of formula I and I' is provided wherein:
R¹ is $C_{1-6}$alkyl or benzyl optionally substituted by one or two groups chosen from halogen, cyano, nitro, hydroxy, $C_{1-4}$alkyl, $C_{2-4}$alkenyl, $C_{2-4}$alkynyl, $C_{1-4}$alkoxy and amino;
R² and R³ are both $(CH_2)_pQ^1$ wherein $Q^1$ is phenyl, pyridyl or furyl optionally substituted by one or two groups independently chosen from:
(a) halogen,
(b) hydroxy,
(c) $C_{1-3}$alkyl, $C_{2-3}$alkenyl and $C_{2-3}$alkynyl,
(d) $C_{1-3}$alkoxy and phenoxy each of which is optionally substituted by up to three halogen atoms,
(e) amino;

R⁴ and R⁵ are independently chosen from $C_{1-6}$alkyl optionally substituted by halogen, hydroxy, amino or $C_{1-4}$alkoxy and $(CH_2)_qQ^2$ wherein $Q^2$ is phenyl optionally substituted by hydroxy, $C_{1-4}$alkyl, $C_{1-4}$alkoxy, thiol, $C_{1-4}$alkylthio, halogen, amino, carboxy, amido, $CO_2H$ and $-NHC(NH_2)_2$;

p is one or two; and q is zero or one.

For the avoidance of doubt each time the moieties $R^6$, $R^7$, $R^8$ and $R^{8'}$ occur more than once in the definition of the compounds of formula (I) they are chosen independently.

As used herein, the expression "$C_{1-10}$alkyl" includes methyl and ethyl groups, and straight-chained and branched propyl, butyl, pentyl and hexyl groups. Particular alkyl groups are methyl, ethyl, n-propyl, isopropyl and t-butyl. Derived expressions such as "$C_{1-6}$alkyl", "$C_{1-4}$alkyl", "$C_{2-10}$alkenyl", "$C_{2-4}$alkenyl", "$C_{2-10}$alkynyl and "$C_{2-4}$alkynyl" are to be construed in an analogous manner.

The expression "$C_{3-7}$cycloalkyl" as used herein includes cyclic propyl, butyl, pentyl, hexyl and heptyl groups such as cyclopropyl and cyclohexyl.

The term "heterocyclic" includes rings which are saturated, partially saturated or unsaturated. Unsaturated heterocyclic rings are also known as heteroaromatic rings.

Suitable 5- and 6-membered heteroaromatic rings include pyridinyl, pyridazinyl, pyrimidinyl, pyrazinyl, pyrrolyl, pyrazolyl, oxazolyl, isoxazolyl, thiazolyl, isothiazolyl, imidazolyl, oxadiazolyl and thiadiazolyl groups. A suitable 5-membered heteroaromatic ring containing four nitrogen atoms is tetrazolyl. Suitable 6-membered heteroaromatic rings containing three nitrogen atoms include 1,2,4-triazine and 1,3,5-triazine. Suitable saturated heterocyclic rings include piperazine, morpholine, piperidine, tetrahydrofuran and tetrahydrothiophene. Tetrahydrofuran is preferred.

The term "halogen" as used herein includes fluorine, chlorine, bromine and iodine, of which fluorine and chlorine and particularly chlorine is/are preferred.

As used herein the term "$C_{1-4}$alkoxy" includes methoxy and ethoxy groups, and straight-chained, branched and cyclic propoxy and butoxy groups, including cyclopropylmethoxy.

Specific Examples according to the present invention include:

L-phenylalaninamide, N-[[[3-[[(1,1-dimethylethoxy)carbonyl]amino]-2-hydroxy-4-phenylbutyl](phenylmethyl)amino]carbonyl]-L-leucyl-, [R-(R*,S*)]-;

L-phenylalaninamide, N-[[[3-[[(benzyloxy)carbonyl]amino]-2-hydroxy-4-phenylbutyl](phenylmethyl)amino]carbonyl]-L-leucyl-, [R-(R*,S*)]-;

L-phenylalaninamide, N-[[[3-[[(benzyloxy)carbonyl]amino]-2-hydroxy-4-phenylbutyl](phenylethyl)amino]carbonyl]-L-leucyl-, [R-(R*,S*)]-;

L-phenylalaninamide, N-[[[3-[[(benzyloxy)carbonyl]amino]-2-hydroxy-4-phenylbutyl][(4-phenoxyphenyl)ethyl]amino]carbonyl]-L-leucyl-, [R-(R*,S*)]-;

L-phenylalaninamide, N-[[[3-[[(benzyloxy)carbonyl]amino]-2-hydroxy-4-phenylbutyl][(4-chlorophenyl)methyl]amino]carbonyl]-L-leucyl-, [R-(R*,S*)]-;

L-phenylalaninamide, N-[[[3-[[(benzyloxy)carbonyl]amino]-2-hydroxy-4-phenylbutyl][(3-chlorophenyl)methyl]amino]carbonyl]-L-leucyl-, [R-(R*,S*)]-;

L-phenylalaninamide, N-[[[3-[[(benzyloxy)carbonyl]amino]-2-hydroxy-4-phenylbutyl][(2-chlorophenyl)methyl]amino]carbonyl]-L-leucyl-, [R-(R*,S*)]-;

L-phenylalaninamide, N-[[[3-[[(benzyloxy)carbonyl]amino]-2-hydroxy-4-phenylbutyl][(2-pyridyl)ethyl]amino]carbonyl]-L-leucyl-, [R-(R*,S*)]-;

L-phenylalaninamide, N-[[[3-[[(benzyloxy)carbonyl]amino]-2-hydroxy-4-phenylbutyl][(2-furyl)methyl]amino]carbonyl]-L-leucyl-, [R-(R*,S*)]-;

L-phenylalaninamide, N-[[[3-[[(benzyloxy)carbonyl]amino]-2-hydroxy-4-phenylbutyl][(4-trifluoromethoxyphenyl)methyl]amino]carbonyl]-L-leucyl-, [R-(R*,S*)]-;

L-phenylalaninamide, N-[[[3-[[(benzyloxy)carbonyl]amino]-2-hydroxy-4-phenylbutyl](phenylethyl)amino]carbonyl]-L-phenylalanyl-, [R-(R*,S*)]-;

L-phenylalaninamide, N-[[[3-[[(benzyloxy)carbonyl]amino]-2-hydroxy-4-phenylbutyl](phenylethyl)amino]carbonyl]-L-norleucyl-, [R-(R*,S*)]-;

L-phenylalaninamide, N-[[[3-[[(benzyloxy)carbonyl]amino]-2-hydroxy-4-phenylbutyl](phenylethyl)amino]carbonyl]-L-norvalyl-, [R-(R*,S*)]-;

L-phenylalaninamide, N-[[[3-[[(benzyloxy)carbonyl]amino]-2-hydroxy-4-phenylbutyl](phenylethyl)amino]carbonyl]-L-phenylglycyl-, [R-(R*,S*)]-;

L-phenylalaninamide, N-[[[3-[[(benzyloxy)carbonyl]amino]-2-hydroxy-4-phenylbutyl](phenylethyl)amino]carbonyl]-L-alanyl-, [R-(R*,S*)]-;

L-phenylalaninamide, N-[[[3-[[(benzyloxy)carbonyl]amino]-2-hydroxy-4-phenylbutyl](phenylethyl)amino]carbonyl]-L-isoleucyl-, [R-(R*,S*)]-;

L-phenylalaninamide, N-[[[3-[[(benzyloxy)carbonyl]amino]-2-hydroxy-4-phenylbutyl](phenylethyl)amino]carbonyl]-L-valyl-, [R-(R*,S*)]-;

L-leucinamide, N-[[[3-[[(benzyloxy)carbonyl]amino]-2-hydroxy-4-phenylbutyl](phenylethyl)amino]carbonyl]-L-leucyl-, [R-(R*,S*)]-;

L-norleucinamide, N-[[[3-[[(benzyloxy)carbonyl]amino]-2-hydroxy-4-phenylbutyl](phenylethyl)amino]carbonyl]-L-leucyl-, [R-(R*,S*)]-;

L-norvalinamide, N-[[[3-[[(benzyloxy)carbonyl]amino]-2-hydroxy-4-phenylbutyl](phenylethyl)amino]carbonyl]-L-leucyl-, [R-(R*,S*)]-;

L-phenylglycinamide, N-[[[3-[[(benzyloxy)carbonyl]amino]-2-hydroxy-4-phenylbutyl](phenylethyl)amino]carbonyl]-L-leucyl-, [R-(R*,S*)]-;

D-leucinamide, N-[[[3-[[(benzyloxy)carbonyl]amino]-2-hydroxy-4-phenylbutyl](phenylethyl)amino]carbonyl]-L-leucyl-, [R-(R*,S*)]-;

L-alaninamide, N-[[[3-[[(benzyloxy)carbonyl]amino]-2-hydroxy-4-phenylbutyl](phenylethyl)amino) carbonyl]-L-leucyl-, [R-(R*,S*)]-;

L-isoleucinamide, N-[[[3-[[(benzyloxy)carbonyl]amino]-2-hydroxy-4-phenylbutyl](phenylethyl)amino]carbonyl]-L-leucyl-, [R-(R*,S*)]-;

L-valinamide, N-[[[3-[[(benzyloxy)carbonyl]amino]-2-hydroxy-4-phenylbutyl](phenylethyl)amino]carbonyl]-L-leucyl-, [R-(R*,S*)]-;

L-leucinamide, N-[[[3-[[(benzyloxy)carbonyl]amino]-2-hydroxy-4-phenylbutyl](phenylethyl)amino]carbonyl]-, (R-(R*,S*)]-;

L-phenylglycinamide, N-[[[3-[[(benzyloxy)carbonyl]amino]-2-hydroxy-4-phenylbutyl](phenylethyl)amino]carbonyl]-, [R-(R*,S*)]-;

L-isoleucinamide, N-[[[3-[[(benzyloxy)carbonyl]amino]-2-hydroxy-4-phenylbutyl](phenylethyl)amino]carbonyl]-, [R-(R*,S*)]- and the pharmaceutically acceptable salts thereof.

Examples of pharmaceutically acceptable salts are hydrochlorides, sulfates, citrates, tartrates, acetates, methanesulfonates, phosphates, oxalates and benzoates.

The compounds of the present invention have an activity as inhibitors of γ secretase. In a preferred embodiment the compounds of the invention inhibit proteolysis of PS-1.

The invention also provides pharmaceutical compositions comprising one or more compounds of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums or surfactants such as sorbitan monooleate, polyethylene glycel, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The present invention also provides a compound of the invention or a pharmaceutically acceptable salt thereof for use in a method of treatment of the human body. Preferably the treatment is for a condition associated with the deposition of β-amyloid. Preferably the condition is a neurological disease having associated β-amyloid deposition such as Alzheimer's disease.

The present invention further provides the use of a compound of the present invention or a pharmaceutically acceptable salt thereof in the manufacture of a medicament for treating or preventing Alzheimer's disease.

Also disclosed is a method of treatment of a subject suffering from or prone to Alzheimer's disease which comprises administering to that subject an effective amount of a compound according to the present invention or a pharmaceutically acceptable salt thereof.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

For treating or preventing Alzheimer's Disease, a suitable dosage level is about 0.01 to 250 mg/kg per day, preferably about 0.01 to 100 mg/kg per day, and especially about 0.01 to 5 mg/kg of body weight per day. The compounds may be administered on a regimen of 1 to 4 times per day. In some cases, however, dosage outside these limits may be used.

tive HPLC, and the mass spectrometer was operated with an APcI probe in positive ionization mode. Solvent was removed from the resulting purified samples by lyophilization.

All products V were analyzed by analytical LC-MS utilizing diode array detection (210–250 nm) and APcI detection (150–850 amu) using a full 5%→95% MeCN gradient with 0.1% aqueous TFA. A strong M+Na$^+$ peak was observed in the mass spectrum in each case.

Conversion of VI→II 0.20 mmol of the amine $R^3$—$NH_2$ was weighed into a test tube, treated with 0.067 mmol of the epoxide VI [$R^1$=tert-butyl, $R^2$=benzyl, CAS RN 98737-29-2; $R^2$=benzyl, CAS RN 128018-44-0] in 0.5 ml of isopropyl alcohol, and heated at 65° C. for 16 h in a test tube heating block. The sample was allowed to cool, concentrated (SPEED VAC™, a concentrator), dissolved in DMSO (0.5 ml) and purified by mass-directed preparative HPLC to give the desired com-

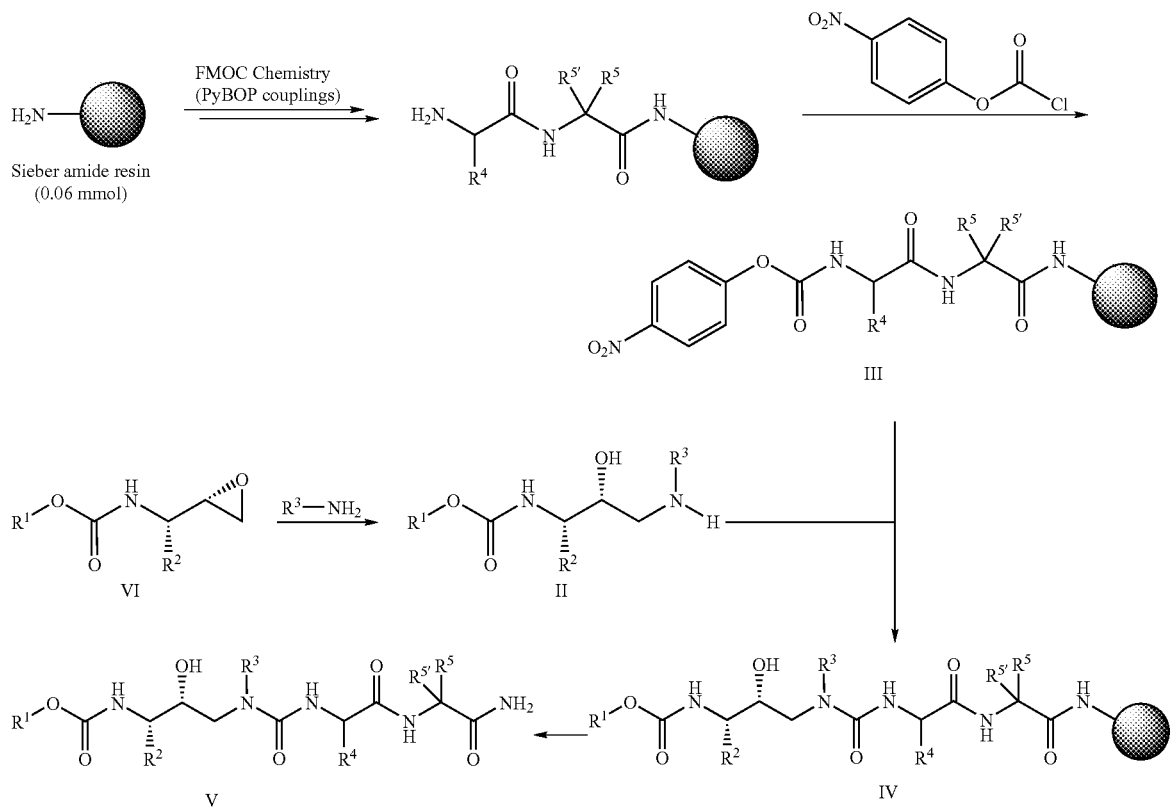

General Procedures

Parallel synthesis techniques were used for the synthesis of all compounds. Solid phase chemistry was carried out using a Quest 210 synthesizer [Argonaut Technologies, Inc]. Where stated, purification by mass-directed preparative HPLC refers to preparative reversed phase HPLC using a Platform LCZ mass spectrometer running under MassLynx 3.3/FractionLynx control [Micromass, UK] to trigger fraction collection when a compound of the molecular weight corresponding to the desired compound was detected. A generic acetonitrile/water gradient of 20%→100% with a constant 0.1% trifluoroacetic acid was used for the preparapound II as its trifluoroacetate salt. This was used directly in reaction with III to give IV as indicated below.

Synthesis of Compounds V 50 mg (0.030 mmol) of FMOC-Sieber amide resin was placed in a Quest 210 solid phase reactor and treated with piperidine/DMF (0.5 ml; 1:1 mixture) with mixing for 30 min. The reactor was drained and washed with DMA (10×1 ml).

Step 1

1 ml of a 0.1 M solution of FMOC—NH—CH($R^5$)—COOH in DMA was added to the reactor followed by 0.2 ml of a DMA mixed solution of HOBT and Hunig's base (0.5

M in both) and 0.5 ml of a 0.2 M solution of PyBOP in DMA. The reactor was mixed for 60 minutes, drained, and washed with DMA (10×1 ml). The reactor was treated with piperidine/DMF (0.5 ml; 1:1 mixture) and mixed for 30 minutes. The reactor was drained and washed with DMA (10×1 ml).

Step 2

1 ml of a 0.1 M solution of FMOC—NH—CH($R^4$)—COOH in DMA was added to the reactor followed by 0.2 ml of a DMA mixed solution of HOBT and Hunig's base (0.5 M in both) and 0.5 ml of a 0.2 M solution of PyBOP in DMA. The reactor was mixed for 60 minutes, drained, and washed with DMA (10×1 ml). The reactor was treated with piperidine/DMF (0.5 ml; 1:1 mixture) and mixed for 30 minutes. The reactor was drained and washed with DMA (10×1 ml).

Step 3

The reactor was washed with 1,2-dichloroethane (DCE) (10×1 ml) and treated with 1.0 nil of a mixed solution of p-nitrophenylchloroformate and Hünigs base (0.1 M in each) in THF/DCE (1:1). The reactor was mixed for 60 min, drained, and washed with DCE (10×1 ml) to give III.

Step 4

The reactor was washed with DMA (10×1.0 ml) and treated with the appropriate amine II in 1.0 ml of DMA containing Hünigs base (0.2 M). The reactor was mixed for 16 h, drained, and washed with DMA (5×1.0 ml), MeOH (2×1.0 ml) and DCE (10×1.0 ml) to give IV.

Step 5

The reactor was treated with 0.5 ml of a 1% solution of TFA in DCM and allowed to stand for 30 min. The reactor was drained into a test tube. Five further identical treatments with TFA were carried out. The resulting filtrate was concentrated and the crude product purified by mass-directed preparative HPLC to give the claimed compound V.

Compounds of formulae $R^3$—$NH_2$ and VI are commercially available or known in the prior art or can be made from commercially available or known compounds by standard methods.

It will be understood that any compound of formula I initially obtained from the above process may, where appropriate, subsequently be elaborated into a further compound of formula I by techniques known from the art. For example compounds in which $R^{5'}$ is hydrogen can be converted into compounds where $R^5$ and $R^{5'}$ together form an oxo group by standard oxidation reactions.

It will also be appreciated that where more than one isomer can be obtained from a reaction then the resulting mixture of isomers can be separated by conventional means.

Where the above-described process for the preparation of the compounds according to the invention gives rise to mixtures of stereoisomers, these isomers may be separated by conventional techniques such as preparative chromatography. The novel compounds may be prepared in racemic form, or individual enantiomers may be prepared either by enantiospecific synthesis or by resolution.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

A typical assay which can be used to determine the level of activity of compounds of the present invention is as follows:

(1) Mouse neuroblastoma neuro 2a cells expressing human app695 are cultured at 50–70% confluency in the presence of sterile 10 mM sodium butyrate.

(2) Cells are placed in 96-well plates at 30,000/well/100 µL in minimal essential medium (MEM) (phenol red-free)+ 10% foetal bovine serum (FBS), 50 mM HEPES buffer (pH 7.3), 1% glutamine, 0.2 mg/ml G418 antibiotic, 10 mM sodium butyrate.

(3) Make dilutions of the compound plate. Dilute stock solution to 5.5% DMSO/110 µM compound. Mix compounds vigorously and store at 4° C. until use.

(4) Add 10 µL compound/well. Mix plate briefly, and leave for 18 h in 37° C. incubator.

(5) Remove 90 µL of culture supernatant and dilute 1:1 with ice-cold 25 mM HEPES (pH 0.3), 0.1% BSA, 1.0 mM EDTA (+broad spectrum protease inhibitor cocktail; pre-aliquotted into a 96-well plate). Mix and keep on ice or freeze at −80° C.

(6) Add back 100 µL of warm MEM+10% FBS, 50 mM HEPES (pH 7.3), 1% glutamine, 0.2 mg/ml G418, 10 mM sodium butyrate to each well, and return plate to 37° C. incubator.

(7) Prepare reagents necessary to determine amyloid peptide levels, for example by ELISA assay (8) To determine if compounds are cytotoxic cell viability following compound administration is assessed by the use of redox dye reduction. A typical example is a combination of redox dye MTS (Promega) and the electron coupling reagent PES. This mixture is made up according to the manufacturer's instructions and left at room temperature.

(9) Quantitate amyloid beta 40 and 42 peptides using an appropriate volume of diluted culture medium by standard ELISA techniques.

(10) Add 15 µL/well MTS/PES solution to the cells; mix and leave at 37° C.

(11) Read plate when the absorbance values are approximately 1.0 (mix briefly before reading to disperse the reduced formazan product).

The Examples of the present invention all had an $ED_{50}$ of less than 500 nM, preferably less than 200 nM and most preferably less than 100 nM in the above assay.

The following examples, made by the above method, illustrate the present invention.

EXAMPLE 1

L-phenylalaninamide, N-[[[3-[[(1,1-dimethylethoxy) carbonyl]amino]-2-hydroxy-4-phenylbutyl](phenylmethyl)amino]carbonyl]-L-leucyl-, [R-(R*,S*)]- m/z 696.4 (M+Na)$^+$

EXAMPLE 2

L-phenylalaninamide, N-[[[3-[[(benzyloxy)carbonyl]amino]-2-hydroxy-4-phenylbutyl](phenylmethyl)amino]carbonyl]-L-leucyl-, [R-(R*,S*)]- m/z 730.4 (M+Na)$^+$

EXAMPLE 3

L-phenylalaninamide, N-[[[3-[[(benzyloxy)carbonyl]amino]-2-hydroxy-4-phenylbutyl](phenylethyl)amino]carbonyl]-L-leucyl-, [R-(R*,S*)]- m/z 744.4 (M+Na)$^+$

EXAMPLE 4

L-phenylalaninamide, N-[[[3-[[(benzyloxy)carbonyl]amino]-2-hydroxy-4-phenylbutyl][(4-phenoxyphenyl)ethyl]amino]carbonyl]-L-leucyl-, [R-(R*,S*)]- m/z 836.4 (M+Na)$^+$

EXAMPLE 5

L-phenylalaninamide, N-[[[3-[[(benzyloxy)carbonyl]amino]-2-hydroxy-4-phenylbutyl][(4-chlorophenyl)methyl]amino]carbonyl]-L-leucyl-, [R-(R*,S*)]- m/z 764.3 (M+Na)$^+$

EXAMPLE 6

L-phenylalaninamide, N-[[[3-[[(benzyloxy)carbonyl]amino]-2-hydroxy-4-phenylbutyl][(3-chlorophenyl)methyl]amino]carbonyl]-L-leucyl-, [R-(R*,S*)]- m/z 764.3 (M+Na)$^+$

EXAMPLE 7

L-phenylalaninamide, N-[[[3-[[(benzyloxy)carbonyl]amino]-2-hydroxy-4-phenylbutyl][(2-chlorophenyl)methyl]amino]carbonyl]-L-leucyl-, [R-(R*,S*)]- m/z 764.3 (M+Na)$^+$

EXAMPLE 8

L-phenylalaninamide, N-[[[3-[[(benzyloxy)carbonyl]amino]-2-hydroxy-4-phenylbutyl][(2-pyridyl)ethyl]amino]carbonyl]-L-leucyl-, [R-(R*,S*)]- m/z 745.4 (M+Na)$^+$

EXAMPLE 9

L-phenylalaninamide, N-[[[3-[[(benzyloxy)carbonyl]amino]-2-hydroxy-4-phenylbutyl][(2-furyl)methyl]amino]carbonyl]-L-leucyl-, [R-(R*,S*)]- m/z 720.4 (M+Na)$^+$

EXAMPLE 10

L-phenylalaninamide, N-[[[3-[[(benzyloxy)carbonyl]amino]-2-hydroxy-4-phenylbutyl][(4-trifluoromethoxyphenyl)methyl]amino]carbonyl]-L-leucyl-, [R-(R*,S*)]- m/z 814.4 (M+Na)$^+$

EXAMPLE 11

L-phenylalaninamide, N-[[[3-[[(benzyloxy)carbonyl]amino]-2-hydroxy-4-phenylbutyl](phenylethyl)amino]carbonyl]-L-phenylalanyl-, [R-(R*,S*)]- m/z 778.4 (M+Na)$^+$

EXAMPLE 12

L-phenylalaninamide, N-[[[3-[[(benzyloxy)carbonyl]amino]-2-hydroxy-4-phenylbutyl](phenylethyl)amino]carbonyl]-L-norleucyl-, [R-(R*,S*)]- m/z 744.4 (M+Na)$^+$

EXAMPLE 13

L-phenylalaninamide, N-[[[3-[[(benzyloxy)carbonyl]amino]-2-hydroxy-4-phenylbutyl](phenylethyl)amino]carbonyl]-L-norvalyl-, [R-(R*,S*)]- m/z 730.4 (M+Na)$^+$

EXAMPLE 14

L-phenylalaninamide, N-[[[3-[[(benzyloxy)carbonyl]amino]-2-hydroxy-4-phenylbutyl](phenylethyl)amino]carbonyl]-L-phenylglycyl-, [R-(R*,S*)]- m/z 764.4 (M+Na)$^+$

EXAMPLE 15

L-phenylalaninamide, N-[[[3-[[(benzyloxy)carbonyl]amino]-2-hydroxy-4-phenylbutyl](phenylethyl)amino]carbonyl]-L-alanyl-, [R-(R*,S*)]- m/z 702.3 (M+Na)$^+$

EXAMPLE 16

L-phenylalaninamide, N-[[[3-[[(benzyloxy)carbonyl]amino]-2-hydroxy-4-phenylbutyl](phenylethyl)amino]carbonyl]-L-isoleucyl-, [R-(R*,S*)]- m/z 744.4 (M+Na)$^+$

EXAMPLE 17

L-phenylalaninamide, N-[[[3-[[(benzyloxy)carbonyl]amino]-2-hydroxy-4-phenylbutyl](phenylethyl)amino]carbonyl]-L-valyl-, [R-(R*,S*)]- m/z 730.4 (M+Na)$^+$

EXAMPLE 18

L-leucinamide, N-[[[3-[[(benzyloxy)carbonyl]amino]-2-hydroxy-4-phenylbutyl](phenylethyl)amino]carbonyl]-L-leucyl-, [R-(R*,S*)]- m/z 710.4 (M+Na)$^+$

EXAMPLE 19

L-norleucinamide, N-[[[3-[[(benzyloxy)carbonyl]
amino]-2-hydroxy-4-phenylbutyl](phenylethyl)
amino]carbonyl]-L-leucyl-, [R-(R*,S*)]- m/z 710.4 (M+Na)$^+$

EXAMPLE 20

L-norvalinamide, N-[[[3-[[(benzyloxy)carbonyl]
amino]-2-hydroxy-4-phenylbutyl](phenylethyl)
amino]carbonyl]-L-leucyl-, [R-(R*,S*)]- m/z 696.4 (M+Na)$^+$

EXAMPLE 21

L-phenylglycinamide, N-[[[3-[[(benzyloxy)carbonyl]amino]-2-hydroxy-4-phenylbutyl](phenylethyl)
amino]carbonyl]-L-leucyl-, [R-(R*,S*)]- m/z 730.4 (M+Na)$^+$

EXAMPLE 22

D-leucinamide, N-[[[3-[[(benzyloxy)carbonyl]
amino]-2-hydroxy-4-phenylbutyl](phenylethyl)
amino]carbonyl]-L-leucyl-, [R-(R*,S*)]- m/z 710.4 (M+Na)$^+$

EXAMPLE 23

L-alaninamide, N-[[[3-[[(benzyloxy)carbonyl]
amino]-2-hydroxy-4-phenylbutyl](phenylethyl)
amino]carbonyl]-L-leucyl-, [R-(R*,S*)]- m/z 668.4 (M+Na)$^+$

EXAMPLE 24

L-isoleucinamide, N-[[[3-[[(benzyloxy)carbonyl]
amino]-2-hydroxy-4-phenylbutyl](phenylethyl)
amino]carbonyl]-L-leucyl-, [R-(R*,S*)]- m/z 710.4 (M+Na)$^+$

EXAMPLE 25

L-valinamide, N-[[[3-[[(benzyloxy)carbonyl]
amino]-2-hydroxy-4-phenylbutyl](phenylethyl)
amino]carbonyl]-L-leucyl-, [R-(R*,S*)]- m/z 696.4 (M+Na)$^+$

EXAMPLE 26

L-leucinamide, N-[[[3-[[(benzyloxy)carbonyl]
amino]-2-hydroxy-4-phenylbutyl](phenylethyl)
amino]carbonyl]-, [R-(R*,S*)]- m/z 597.3 (M+Na)$^+$

EXAMPLE 27

L-phenylglycinamide, N-[[[3-[[(benzyloxy)carbonyl]amino]-2-hydroxy-4-phenylbutyl](phenylethyl)
amino]carbonyl]-, [R-(R*,S*)]- m/z 617.3 (M+Na)$^+$

EXAMPLE 28

L-isoleucinamide, N-[[[3-[[(benzyloxy)carbonyl]
amino]-2-hydroxy-4-phenylbutyl](phenylethyl)
amino]carbonyl]-, [R-(R*,S*)]- m/z 597.3 (M+Na)$^+$

The invention claimed is:

1. A compound of formula I or a pharmaceutically acceptable salt thereof:

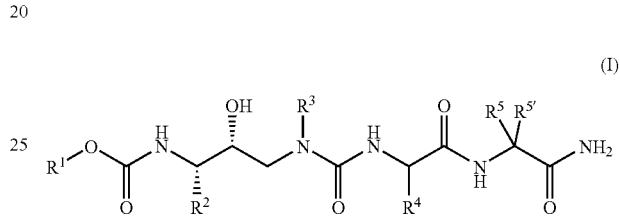

wherein:
$R^1$ is (1) $C_{1-10}$alkyl, $C_{2-10}$alkenyl or $C_{2-10}$alkynyl,
wherein said alkyl, alkenyl and alkynyl is optionally
substituted with one to three substituents independently
chosen from:
  (i) hydroxy;
  (ii) carboxy;
  (iii) halogen;
  (iv) $C_{1-4}$alkoxy;
  (v) $C_{1-4}$alkoxycarbonyl;
  (vi) —NR$^6$R$^7$ wherein R$^6$ and R$^7$ are independently
  chosen from hydrogen, $C_{1-5}$alkyl and $C_{1-5}$alkoxy
  $C_{1-5}$alkyl;
  (vii) —CONR$^6$R$^7$ or OCONR$^6$R$^7$;
  (viii) —N(R$^8$)QR$^9$ wherein:
    Q is C(O), C(S), SO$_2$ or C(NH);
    R$^8$ is hydrogen or $C_{1-4}$alkyl; and
    R$^9$ is hydrogen, $C_{1-4}$alkyl, $C_{1-4}$alkoxy, amino,
    $C_{1-4}$alkylamino, or di($C_{1-4}$alkyl)amino wherein
    each alkyl group is independently chosen;
  (ix) $C_{3-7}$cycloalkyl; or
  (x) phenyl; naphthyl; a five-membered heterocyclic
  ring containing 1, 2, 3 or 4 heteroatoms independently chosen from O, N and S, at most one of the
  heteroatoms being O or S; or a six-membered heterocyclic ring containing 1, 2 or 3 nitrogen atoms;
  wherein said phenyl, naphthyl or five or six-membered heterocyclic ring is optionally substituted by
  one to three groups independently chosen from:
    (a) halogen, cyano and nitro,
    (b) hydroxy,
    (c) $C_{1-4}$alkyl, $C_{2-4}$alkenyl and $C_{2-4}$alkynyl,
    (d) $C_{1-4}$alkoxy,
    (e) NR$^6$R$^7$,
    (f) CO$_2$R$^8$,
    (g) CONR$^6$R$^7$ or OCONR$^6$R$^7$,
    (h) SO$_2$NR$^6$R$^7$,

17

(i) CH$_2$NR$^6$R$^7$,
(j) N(R$^8$)COR$^8$, and
(k) NR$^8$SO$_2$R$^8$;

or (2) phenyl; naphthyl; a five-membered heterocyclic ring containing 1, 2, 3 or 4 heteroatoms independently chosen from O, N and S, at most one of the heteroatoms being O or S; a six-membered heterocyclic ring containing 1, 2 or 3 nitrogen atoms; wherein said phenyl, naphthyl or five or six-membered heterocyclic ring is optionally substituted by one to three groups independently chosen from:

(a) halogen, cyano and nitro,
(b) hydroxy,
(c) C$_{1-4}$alkyl, C$_{2-4}$alkenyl and C$_{2-4}$alkynyl,
(d) C$_{1-4}$alkoxy,
(e) NR$^6$R$^7$,
(f) CO$_2$R$^8$,
(g) CONR$^6$R$^7$ or OCONR$^6$R$^7$,
(h) SO$_2$NR$^6$R$^7$,
(i) CH$_2$NR$^6$R$^7$,
(j) N(R$^8$)COR$^{8'}$, and
(k) NR$^8$SO$_2$R$^8$;

R$^2$ and R$^3$ are independently chosen from C$_{1-10}$alkyl, C$_{1-10}$alkoxy, C$_{2-10}$alkenyl, C$_{2-10}$alkenyloxy, C$_{2-10}$alkynyl or C$_{2-10}$alkynyloxy; phenyl; naphthyl; a five-membered heteroaromatic ring containing 1, 2, 3 or 4 heteroatoms independently chosen from O, N and S, at most one of the heteroatoms being O or S; a six-membered heteroaromatic ring containing 1, 2 or 3 nitrogen atoms; and a group (CH$_2$)$_p$Q$^1$ wherein Q$^1$ is phenyl, naphthyl, a five-membered heteroaromatic ring containing 1, 2, 3 or 4 heteroatoms independently chosen from O, N and S, at most one of the heteroatoms being O or S, and a six-membered heteroaromatic ring containing 1, 2 or 3 nitrogen atoms; and wherein each of R$^2$ and R$^3$ is independently optionally substituted by one to three groups independently chosen from:

(a) halogen, cyano and nitro,
(b) hydroxy,
(c) C$_{1-6}$alkyl, C$_{2-6}$ alkenyl and C$_{2-6}$alkynyl,
(d) C$_{1-6}$alkoxy and phenoxy each of which is optionally substituted by one to three halogen atoms,
(e) NR$^6$R$^7$,
(f) CO$_2$R$^8$,
(g) CONR$^6$R$^7$ or OCONR$^6$R$^7$,
(h) SO$_2$NR$^6$R$^7$,
(i) CH$_2$NR$^6$R$^7$,
(j) N(R$^8$)COR$^{8'}$,
(k) NR$^8$SO$_2$R$^8$;

alternatively R$^3$ may be hydrogen;

R$^4$ and R$^5$ are independently chosen from hydrogen, C$_{1-6}$alkyl optionally substituted by halogen, hydroxy, thiol, amino, C$_{14}$alkoxy, C$_{14}$ alkylthio, carboxy, C$_{1-4}$ alkoxycarbonyl and (CH$_2$)$_q$Q$^2$ wherein Q$^2$ is a five-membered unsaturated heterocycle containing 1, 2, 3 or 4 heteroatom optionally chosen from O, N, and S providing that not more than one heteroatom is O or S, a six-membered unsaturated heterocycle containing 1, 2 or 3 N atoms, phenyl, naphthyl or a fused ring which is indolyl, each of the foregoing rings being optionally substituted with one to three groups independently chosen from hydroxy, C$_{1-4}$alkyl, C$_{1-4}$alkoxy, thiol, C$_{1-4}$alkylthio, halogen, amino, carboxy, amido, CO$_2$H and —NHC(NH$_2$)$_2$; and R$^{5'}$ is a hydrogen atom;

alternatively R$^5$ and R$^{5'}$ together represent an oxo group;

18 p is zero, one, two or three; and
q is zero, one, two or three;
with the proviso that no carbon atom is substituted by more than one hydroxy group.

2. A compound according to claim 1 of formula I' or formula I":

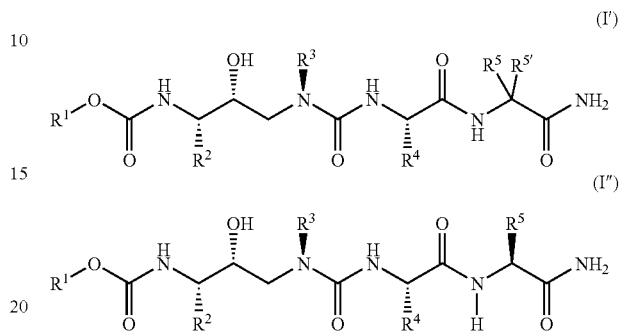

or a pharmaceutically acceptable salt thereof.

3. The compound of claim 1 wherein:

R$^1$ is C$_{1-6}$alkyl or benzyl optionally substituted by one or two groups chosen from halogen, cyano, nitro, hydroxy, C$_{1-4}$alkyl, C$_{2-4}$alkenyl, C$_{2-4}$alkynyl, C$_{1-4}$alkoxy and amino;

R$^2$ and R$^3$ are both (CH$_2$)$_q$Q$^1$ wherein Q$^1$ is phenyl, pyridyl or furyl optionally substituted by one or two groups independently chosen from:

(a) halogen,
(b) hydroxy,
(c) C$_{1-3}$alkyl, C$_{2-3}$alkenyl and C$_{2-3}$alkynyl,
(d) C$_{1-3}$alkoxy and phenoxy each of which is optionally substituted by up to three halogen atoms,
(e) amino;

R$^4$ and R$^5$ are independently chosen from C$_{1-6}$alkyl optionally substituted by halogen, hydroxy, amino or C$_{1-4}$alkoxy and (CH$_2$)$_q$Q$^2$ wherein Q$^2$ is phenyl optionally substituted by hydroxy, C$_{1-4}$alkyl, C$_{1-4}$alkoxy, thiol, C$_{1-4}$alkylthio, halogen, amino, carboxy, amido, CO$_2$H and NHC(NH$_2$)$_2$;

p is one or two; and
q is zero or one.

4. A compound which is selected from the group consisting of:

L-phenylalaninamide, N-[[[3-[[(1,1-dimethylethoxy)carbonyl]amino]-2-hydroxy-4-phenylbutyl](phenylmethyl)amino]carbonyl]-L-leucyl-, [R-(R*,S*)]-;

L-phenylalaninamide, N-[[[3-[[(benzyloxy)carbonyl]amino]-2-hydroxy-4-phenylbutyl](phenylmethyl)amino]carbonyl]-L-leucyl-, [R-(R*,S*)]-;

L-phenylalaninamide, N-[[[3-[[(benzyloxy)carbonyl]amino]-2-hydroxy-4-phenylbutyl](phenylethyl)amino]carbonyl]-L-leucyl-, [R-(R*,S*)]-;

L-phenylalaninamide, N-[[[3-[[(benzyloxy)carbonyl]amino]-2-hydroxy-4-phenylbutyl][(4-phenoxyphenyl)ethyl]amino]carbonyl]-L-leucyl-, [R-(R*,S*)]-;

L-phenylalaninamide, N-[[[3-[[(benzyloxy)carbonyl]amino]-2-hydroxy-4-phenylbutyl][(4-chlorophenyl)methyl]amino]carbonyl]-L-leucyl-, [R-(R*,S*)]-;

L-phenylalaninamide, N-[[[3-[[(benzyloxy)carbonyl]amino]-2-hydroxy-4-phenylbutyl][(3-chlorophenyl)methyl]amino]carbonyl]-L-leucyl-, [R-(R*,S*)]-;

L-phenylalaninamide, N-[[[3-[[(benzyloxy)carbonyl]amino]-2-hydroxy-4-phenylbutyl][(2-chlorophenyl)methyl]amino]carbonyl]-L-leucyl-, [R-(R*,S*)]-;

L-phenylalaninamide, N-[[[3-[[(benzyloxy)carbonyl]amino]-2-hydroxy-4-pbenylbutyl][(2-pyridyl)ethyl]amino]carbonyl]-L-leucyl-, [R-(R*,S*)]-;

L-phenylalaninamide, N-[[[3-[[(benzyloxy)carbonyl]amino]-2-hydroxy-4-phenylbutyl][(2-furyl)methyl]amino]carbonyl]-L-leucyl-, [R-(R*,S*)]-;

L-phenylalaninamide, N-[[[3-[[(benzyloxy)carbonyl]amino]-2-hydroxy-4-phenylbutyl][(4-trifluoromethoxyphenyl)methyl]amino]carbonyl]-L-leucyl-, [R-(R*,S*)]-;

L-phenylalaninamide, N-[[[3-[[(benzyloxy)carbonyl]amino]-2-hydroxy-4-phenylbutyl](phenylethyl)amino]carbonyl]-L-phenylalanyl-, [R-(R*,S*)]-;

L-phenylalaninamide, N-[[[3-[[(benzyloxy)carbonyl]amino]-2-hydroxy-4-phenylbutyl](phenylethyl)amino]carbonyl]-L-norleucyl-, [R-(R*,S*)]-;

L-phenylalaninamide, N-[[[3-[[(benzyloxy)carbonyl]amino]-2-hydroxy-4-phenylbutyl](phenylethyl)amino]carbonyl]-L-norvalyl-, [R-(R*,S*)]-;

L-phenylalaninamide, N-[[[3-[[(benzyloxy)carbonyl]amino]-2-hydroxy-4-phenylbutyl](phenylethyl)amino]carbonyl]-L-phenylglycyl-, [R-(R*,S*)]-;

L-phenylalaninamide, N-[[[3-[[(benzyloxy)carbonyl]amino]-2-hydroxy-4-phenylbutyl](phenylethyl)amino]carbonyl]-L-alanyl-, [R-(R*,S*)]-;

L-phenylalaninamide, N-[[[3-[[(benzyloxy)carbonyl]amino]-2-hydroxy-4-phenylbutyl](phenylethyl)amino]carbonyl]-L-isoleucyl-, [R-(R*,S*)]-;

L-phenylalaninamide, N-[[[3-[[(benzyloxy)carbonyl]amino]-2-hydroxy-4-phenylbutyl](phenylethyl)amino]carbonyl]-L-valyl-, [R-(R*,S*)]-;

L-leucinamide, N-[[[3-[[(benzyloxy)carbonyl]amino]-2-hydroxy-4-phenylbutyl](phenylethyl)amino]carbonyl]-L-leucyl-, [R-(R*,S*)]-;

L-norleucinamide, N-[[[3-[[(benzyloxy)carbonyl]amino]-2-hydroxy-4-phenylbutyl](phenylethyl)amino]carbonyl]-L-leucyl-, [R-(R*,S*)]-;

L-norvalinamide, N-[[[3-[[(benzyloxy)carbonyl]amino]-2-hydroxy-4-phenylbutyl](phenylethyl)amino]carbonyl]-L-leucyl-, [R-(R*,S*)]-;

L-phenylglycinamide, N-[[[3-[[(benzyloxy)carbonyl]amino]-2-hydroxy-4-phenylbutyl](phenylethyl)amino]carbonyl]-L-leucyl-, [R-(R*,S*)]-;

D-leucinamide, N-[[[3-[[(benzyloxy)carbonyl]amino]-2-hydroxy-4-phenylbutyl](phenylethyl)amino]carbonyl]-L-leucyl-, [R-(R*,S*)]-;

L-alaninamide, N-[[[3-[[(benzyloxy)carbonyl]amino]-2-hydroxy-4-phenylbutyl](phenylethyl)amino]carbonyl]-L-leucyl-, [R-(R*,S*)]-;

L-isoleucinamide, N-[[[3-[[(benzyloxy)carbonyl]amino]-2-hydroxy-4-phenylbutyl](phenylethyl)amino]carbonyl]-L-leucyl-, [R-(R*,S*)]-;

L-valinamide, N-[[[3-[[(benzyloxy)carbonyl]amino]-2-hydroxy-4-phenylbutyl](phenylethyl)amino]carbonyl]-L-leucyl-, [R-(R*,S*)]-;

L-leucinamide, N-[[[3-[[(benzyloxy)carbonyl]amino]-2-hydroxy-4-phenylbutyl](phenylethyl)amino]carbonyl]-, [R-(R*,S*)]-;

L-phenylglycinamide, N-[[[3-[[(benzyloxy)carbonyl]amino]-2-hydroxy-4-phenylbutyl](phenylethyl)amino]carbonyl]-, [R-(R*,S*)]-;

L-isoleucinamide, N-[[[3-[[(benzyloxy)carbonyl]amino]-2-hydroxy-4-phenylbutyl](phenylethyl)amino]carbonyl]-, [R-(R*,S*)]- and the pharmaceutically acceptable salts thereof.

5. A pharmaceutical composition comprising a compound of claim 1 and a pharmaceutically acceptable carrier.

6. A method for the treatment of a patient suffering from Alzheimer's disease which comprises administering to the patient an effective amount of a compound of claim 1 or a pharmaceutically acceptable salt thereof.

\* \* \* \* \*